United States Patent [19]

Haber et al.

[11] 4,217,456

[45] Aug. 12, 1980

[54] NITROFURYL QUINALDINIC DERIVATIVES AND PREPARATION THEREOF

[76] Inventors: Raphael R. G. Haber; Eva Schöenberger, both of Givatayim, Israel

[21] Appl. No.: 900,815

[22] Filed: Apr. 27, 1978

Related U.S. Application Data

[62] Division of Ser. No. 643,830, Jun. 6, 1967, Pat. No. 4,087,427.

[30] Foreign Application Priority Data

Jun. 23, 1966 [IL] Israel ............................................ 26022

[51] Int. Cl.$^2$ ............................................ G07D 215/48
[52] U.S. Cl. ...................................... 546/167; 424/258
[58] Field of Search ........ 260/287 G, 287 L, 287 CE; 546/167, 153, 157

[56] References Cited

U.S. PATENT DOCUMENTS

| | | | |
|---|---|---|---|
| 3,349,095 | 10/1967 | Haber et al. | 260/347.8 C |
| 3,352,683 | 11/1967 | Schmidt et al. | 260/287 L |
| 3,374,239 | 3/1968 | Burch | 260/287 G |

OTHER PUBLICATIONS

Hackh's Chemical Dictionary, pp. 8, 134.
Burch; Chem. Abs., vol. 69: 59113s (1968).

*Primary Examiner*—Mary C. Lee
*Attorney, Agent, or Firm*—Ostrolenk, Faber, Gerb & Soffen

[57] ABSTRACT

The present invention relates to new nitrofuryl quinaldinic derivatives, to process for their preparation and to compositions containing said nitrofuryl quinaldinic derivatives.

4 Claims, No Drawings

NITROFURYL QUINALDINIC DERIVATIVES AND PREPARATION THEREOF

This application is a division of application Ser. No. 643,830, filed June 6, 1967, and now U.S. Pat. No. 4,087,427.

The present invention relates to nitrofuryl quinaldinic acids and esters thereof which are substituted in either the 2- or 4- position by a 5-nitrofuryl group, which quinaldinic derivatives can be further substituted, and to the nitrogen oxides and non-toxic acid addition salts of such derivatives.

Suitable substituents with which the new nitrofuryl quinaldinic compounds according to the present invention can be substituted are, for example, lower alkyl ($C_1$-$C_5$) radicals, which may be further substituted, e.g. by halogen atoms (such as chlorine and bromine), lower alkoxy ($C_1$-$C_5$) radicals, hydroxy, acyloxy, acyloxy- or hydroxy methyl and nitro groups, amino groups which may be further substituted, e.g. by substituted or unsubstituted lower alkyl radicals or by acyl radicals; cycloalkyl radicals, and the like. Moreover, the 6- and 7-carbon atoms may together be part of the further aromatic or heteroaromatic nucleus which can also be substituted.

Valuable nitrofuryl quinaldinic derivatives, according to the present invention are, for example, compounds of the general formula I

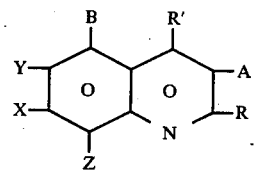

in which R is hydrogen, 5-nitrofuryl, substituted or unsubstituted lower alkyl, acyloxy or hydroxy-methyl, carbonyl or its oxime or one of its hydrazones, or carboxyl or an ester or amide thereof, R' is hydrogen, 5-nitrofuryl, acyloxy- or hydroxy-methyl, or carboxyl, X is hydrogen, halogen, hydroxy or acyloxy, lower alkoxy, a substituted or unsubstituted lower alkyl or amino group, Y is hydrogen or a substituted or unsubstituted alkyl group, Z is hydrogen, halogen, nitro or a substituted or unsubstituted lower alkyl or amino group, A is hydrogen or a substituted or unsubstituted lower alkyl group, B is hydrogen, nitro or a substituted or unsubstituted amino group, and wherein X and Y taken together may constitute part of an aromatic or heteroaromatic nucleus which may be further substituted, wherein one of R and R' is 5-nitrofuryl and at least one of R,R' and X is carboxyl or an ester thereof.

The nitrofuryl quinaldinic derivatives according to the present invention can be prepared by various processes. Thus, certain of the nitrofuryl quinaldinic compounds bearing the 5-nitrofuryl group in the 4-position are prepared by the condensation of a 1-(5'-nitrofuryl)-1,3-diketobutane of the general formula II (described in French Pat. No. 1,443,177).

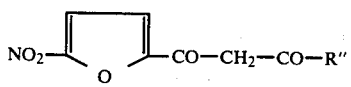

with a primary amine of the formula $H_2NR'''$ to yield an anil of the formula

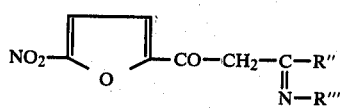

in which R" stands for a substituted or unsubstituted lower alkyl radical and R''' stands for a substituted or unsubstituted phenyl radical, whereafter the anil compound is subjected to a ring closure treatment.

The condensation step is preferably carried out by either melting the reactants together in the presence of a catalyst, e.g. $ZnCl_2$, or by boiling the reactants together with an inert solvent, e.g. isopropanol. The anils are obtained by these methods in nearly theoretical yields.

The ring closure treatment is preferably carried out with concentrated sulfuric acid or with polyphosphoric acid at temperatures between 0° and 180° C. Certain nitrofuryl quinaldinic compounds bearing the 5-nitrofuryl group in the 2-position are prepared by the condensation of a 5-nitrofuryl ketone of the formula IV (The Furans by Dunlop and Peters, ACS Monograph Series 1953—pages 429; 155)

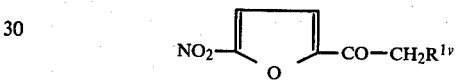

with a compound of the formula V

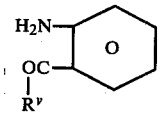

wherein the phenyl nucleus may be further substituted, in which $R^{iv}$ stands for hydrogen or a substituted or unsubstituted lower alkyl group and $R^v$ for hydrogen or a lower alkyl radical in the presence of a catalyst, e.g. $ZnCl_2$, if desired, with the addition of a solvent, e.g., glacial acetic acid.

Further substituents can be introduced into the quinaldinic moiety in any suitable manner at any stage of the above or other processes. Eventually, certain new nitrofuryl quinoline derivatives according to the present invention can be converted into other ones by methods known per se.

Thus, for example, alkyl radicals can be converted into halogenated alkyl radicals by way of halogenation, into a carbonyl group by way of oxidation, e.g. with selenium dioxide, or be converted into a carboxyl group by way of, for example, oxidation, which carboxyl group, in turn, may be esterified.

The carbonyl group may be converted into the oxime by reaction with hydroxylamine and into a hydrazone by reaction with the appropriate hydrazine derivative.

The hydroxy group may be converted into the acyloxy group by way of esterification and vice versa, the acyloxy group may be converted into the hydroxyl group by hydrolysis.

The nitrofuryl derivatives according to the present invention can be ring-nitrated with concentrated nitric acid without destroying either the furan nucleus or the quinoline nuclei.

The nitrofuryl derivatives according to the present invention can be converted into the corresponding nitrogen-oxides and acid-addition salts by methods known per se. Thus, the nitrogen-oxide is prepared by oxidation of the appropriate nitrofuryl derivative with a suitable peroxide, e.g., hydrogen peroxide, and the acid-addition salt by reaction with an appropriate acid.

A suitable process for the preparation of nitrofuryl compounds bearing the 5-nitrofuryl group in the 4-position and an acyloxy group in the 2-position consists in reacting 2-methyl-4-[2'-(5'-nitrofuryl)] quinoline N-oxide with a carboxylic acid anhydride and, if desired, subjecting the product obtained to hydrolysis.

The new nitrofuryl derivatives according to the present invention have excellent antibacterial properties. They are also active antifungal agents and are relatively non-toxic. They can be used as therapeutic agents in human and veterinary fields and as fungicides in agriculture. Due to the broad spectrum activity against various types of bacteria and fungi, the compounds described can be used with advantage in the external treatment of wounds.

The activity of some of the new nitrofuryl derivatives of the present invention is exemplified in the following Table against a gram-positive (*Staph. aureus*), a gram-negative (Salmonella) bacterium and a fungus (*Candida albicans*). The Table indicates the minimum inhibitory concentration of the compound under reference in mg/100 cc required in order to inhibit the growth between 1 and 6 strains of each type. The measurements have been carried out by the conventional tube dilution method at 37° after 24 hours.

| Compound | Staph. aureus | Sal. | Candida albicans |
|---|---|---|---|
| 2-carboxy-4-[2'-(5'-nitrofuryl)] quinoline | 0.1 | >1 | 3–5 |
| 2-methyl-4-[2'-(5'-nitrofuryl)]-7-acetoxy quinoline | 0.005 | 0.2–0.5 | 1 |

The new nitrofuryl derivatives according to the present invention can be prescribed to be taken per se, but are preferably prescribed in the form of tablets, capsules, ampules, ointments, tinctures or solutions, said preparations being prepared in the conventional manner, i.e., by the addition of suitable binders, extenders, emulsifiers, solvents, other suitable therapeutic compounds and the like.

The new nitrofuryl derivatives can also be used as feed additives. They can be either admixed directly with the feed, advantageously in an amount of about 0.001–1% of the total feed or as a part of a pre-mix. Such pre-mix may contain, besides the nitrofuryl derivative, any suitable carrier and/or feed additive, e.g., bentonite, $CaCO_3$, soyabean meal, corn meal, and the like. The pre-mix should contain about 1–95% of the new compound.

The invention will now be illustrated by the following Examples without being limited by them. All temperatures herein are set forth in degrees Centigrade and all melting points are uncorrected.

EXAMPLE I 5.91 g (0.03 mole) of 1-(5'-nitrofuryl)-butane-1,3-dione and 2.8 g (0.03 mole) of freshly distilled aniline were heated together at 120° with a catalytic amount of $ZnCl_2$. A clear melt was obtained and after 15 minutes, the whole mass solidified. The melt was kept for a further 10 minutes at 120° C. and thereafter cooled and recrystallized from methanol to yield crystalline 1-(5'-nitro-2'-furo)-butanone-3-phenylimino. Then 5.6 g (0.02 mole) of the above Schiff base were dissolved at about 5° in 30 g of concentrated sulfuric acid. The clear solution obtained was allowed to reach room temperature and then heated for 10 minutes to 100°–110° and then poured on ice water. An olive green precipitate was obtained, filtered off and suspended in water. Ammonia was added to the suspension until the pH was slightly alkaline, the suspension cooled, and the precipitate obtained was filtered off to yield 2-methyl-4-[2'-(5'-nitrofuryl)] quinoline.

2 g of the 2-methyl-4-[2'-(5'-nitrofuryl)] quinoline were dissolved with heating in 20 ml of glacial acetic acid. 4 g of anhydrous sodium acetate and thereafter 1.25 ml of bromine dissolved in some acetic acid were added at 70°–75°. The reaction mixture was heated for 90 minutes at 90°–95°, cooled and the precipitate obtained was filtered off to yield yellow crystals of 2-tribromomethyl-4-[2'-5'-nitrofuryl)] quinoline.

1.5 g of 2-tribromomethyl-4-[2'-(5'-nitrofuryl)] quinoline were dissolved in 50 ml of 50% sulfuric acid. Catalytic quantities of $FeCl_3$ were added to the solution obtained which was then kept for 20 hours at 110°–130°. The clear solution was cooled, water was added and the precipitate obtained was filtered off to yield 0.4 g of 2-carboxy-4-[2'-(5'-nitrofuryl)] quinoline; m.p. 190°–193°.

An analytical sample was obtained by recrystallization from glacial acetic acid; m.p. 200°. The analsysis was calculated for $C_{14}H_8N_2O_5$:

Calculated: C: 59.16%; H: 2.84%; N: 9.86%. Found: C: 59.21%; H: 2.85%; N: 9.52%.

EXAMPLE 2

1-(5'-nitrofuryl)-2,4-butanedione and m-aminophenol were heated with a catalytic amount of $ZnCl_2$ at 90° to produce 1-(5'-nitro-2'-furo)-butanone-3-(m-hydroxyphenyl) amino. This Schiff base was dissolved in sulfuric acid, the aqueous suspension neutralized with ammonia to precipitate 2-methyl-4-[2'-(5'-nitrofuryl)]-7-hydroxy quinoline.

A mixture of 2 gm of 2-methyl-4-[2'-(5'-nitrofuryl)] 7-hydroxy quinoline, 40 ml of acetic anhydride and 1 ml of concentrated sulfuric acid were refluxed for 2 hours, left to cool to room temperature and finally poured on ice water. After 2 hours of further stirring, the brown crystals obtained were filtered off and washed thoroughly with water. 1.5 g of 2-methyl-4-[2'-(5'-nitrofuryl)]-7-acetoxy-quinoline were obtained; yield 65%.

An analytic sample was prepared by repeating recrystallization from dioxane, nitromethane and isopropanol, m.p. 171.5°–172.5°. The analysis was calculated for $C_{16}H_{12}N_2O_5$:

Calculated: C: 61.54%; H: 3.87%; N: 8.97%. Found: C: 61.37%; H: 3.83%; N: 9.01%.

The N-oxide of this compound was prepared by an oxidation reaction with $H_2O_2$ in glacial acetic acid, m.p. 176°.

EXAMPLE 3

A mixture of 2 g of 2-methyl-4-[2'-(5'-nitrofuryl)] quinoline N-oxide, and 10 g of acetic acid anhydride was heated to 120°–130° for 2 hours on an oil bath. The excess acetic anhydride was distilled off under reduced pressure and ice water was added to the residue. Crystals precipitated which were separated by filtration and washed with water. 2.1 g of 2-acetoxymethyl-4-[2'-(5'-nitrofuryl)] quinoline were obtained; yield 89%; m.p. 125°–130°. After recrystallization from ethanol with charcoal, the melting point rose to 135°–136°.

An analytical sample having a melting point of 137°–138° was prepared. The analysis was calculated for $C_{16}H_{12}N_2O_5$:

Calculated: C: 61.54%; H: 3.87%; N: 8.97%. Found: C: 61.44%; H: 3.92%; N: 9.00%.

The N-oxide of the above compound was prepared by oxidation with hydrogen peroxide dissolved in glacial acetic acid yielding a compound melting at 188°–189.5° after recrystallization from isopropanol.

2-hydroxymethyl-4-[2'-(5'-nitrofuryl)] quinoline was prepared by refluxing the 2-acetoxymethyl-4-[2'-(5'-nitrofuryl)] quinoline in a 12% sulfuric acid solution.

EXAMPLE 4

In the same manner as described in Example 3, there was prepared from 2-methyl-4-[2'-(5'-nitrofuryl)]-7-hydroxy quinoline N-oxide, the 2-acetoxymethyl-4-[2'-(5'-nitrofuryl)]-7-acetoxy quinoline, m.p. 151.5°–152°. The analysis was calculated for $C_{18}H_{14}N_2O_7$:

Calculated: C: 58.38%; H: 3.81%; N: 7.56%. Found: C: 58.41%; H: 4.04%; N: 7.72%.

EXAMPLE 5

A mixture of polyethylene glycol 4000 (200 g), polyethylene glycol 1500 (200 g), polyethylene glycol 300 (250 g), propylene glycol (125 g) and cetyl alcohol (20 g) was heated on a steam bath. 2–3 g of the quinoline compound were added to the melt with stirring. After cooling, the mass obtained was passed through an ointment roller to obtain an ointment.

EXAMPLE 6

16 g of the quinoline compound and 25 g of lactose were mixed together. A starch mucilage binder was added in an amount sufficient to produce a proper mass of granulation. The mass obtained was passed through a sieve, dried at 70°–80° and then again passed through a sieve. A small quantity of talcum and starch powder was added and tablets were pressed in a tabletting machine.

EXAMPLE 7

A mixture of 1 g of the quinoline compound, 4 g of lactose, 6 g of calcium carbonate and 50 g of soyabean meal were mixed in a Fisher-Kendall mixer to be utilized as a premix for animal feedstuffs.

We claim:

1. A quinoline compound of the formula

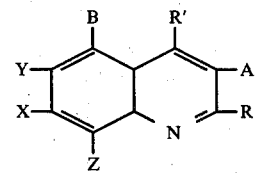

in which R is hydrogen, 5-nitrofuryl, lower alkyl, acetoxy or hydroxy-methyl, carbonyl or its oxime or one of its hydrazones, or carboxyl, R' is hydrogen, 5-nitrofuryl, acetoxy- or hydroxy-methyl, or carboxyl, X is hydrogen, halogen, hydroxy, acetoxy, carboxyl, lower alkoxy, lower alkyl or amino, Y is hydrogen or alkyl, Z is hydrogen, halogen, nitro, lower alkyl or amino, A is hydrogen or lower alkyl group, B is hydrogen, nitro or amino, and, wherein one of R and R' is 5-nitrofuryl and at least one of R,R' and X is carboxyl or an ester thereof; and the N-oxide and non-toxic acid addition sales of such compound.

2. 2-carboxy-4-[2'-(5'-nitrofuryl)] quinoline or its N-oxide according to claim 1.

3. 2-methyl-4-[2'-(5'-nitrofuryl)]-7-acetoxy quinoline or its N-oxide.

4. 2-acetoxymethyl-4-[2'-(5'-nitrofuryl)]-7-acetoxy quinoline or its N-oxide.

* * * * *